US008314696B2

(12) United States Patent
Stut

(10) Patent No.: US 8,314,696 B2
(45) Date of Patent: Nov. 20, 2012

(54) BABY MONITORING SYSTEMS

(75) Inventor: Wilhelmus Johannes Joseph Stut, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 378 days.

(21) Appl. No.: 12/667,239

(22) PCT Filed: Jun. 30, 2008

(86) PCT No.: PCT/IB2008/052626
§ 371 (c)(1),
(2), (4) Date: Dec. 30, 2009

(87) PCT Pub. No.: WO2009/004568
PCT Pub. Date: Jan. 8, 2009

(65) Prior Publication Data
US 2010/0176942 A1 Jul. 15, 2010

(30) Foreign Application Priority Data

Jul. 3, 2007 (EP) .................................... 07111619
Jun. 17, 2008 (EP) .................................... 08158376

(51) Int. Cl.
*G08B 1/08* (2006.01)
*G08B 23/00* (2006.01)
(52) U.S. Cl. ................ 340/539.15; 340/573.1
(58) Field of Classification Search ............ 340/539.15, 340/573.1
See application file for complete search history.

(56) References Cited

U.S. PATENT DOCUMENTS

| 4,061,042 | A  | * | 12/1977 | Hetrich ........................... 73/647 |
| 6,989,744 | B2 | * | 1/2006  | Proebsting ............... 340/539.15 |
| 7,151,444 | B1 | * | 12/2006 | Doyle ........................ 340/539.1 |
| 7,251,334 | B1 | * | 7/2007  | Sundberg ........................ 381/56 |
| 7,642,911 | B2 | * | 1/2010  | Desrosiers et al. ........ 340/539.1 |
| 7,696,888 | B2 | * | 4/2010  | Swan et al. ................ 340/573.1 |
| 2003/0067390 | A1 | * | 4/2003 | Fitzgerald et al. ......... 340/573.1 |
| 2003/0083540 | A1 |   | 5/2003 | Fitzgerald et al. |
| 2006/0103522 | A1 | * | 5/2006 | Spencer .................... 340/539.15 |
| 2006/0197671 | A1 |   | 9/2006 | Groover |
| 2006/0232428 | A1 | * | 10/2006 | Desrosiers et al. ........ 340/573.1 |
| 2007/0156060 | A1 | * | 7/2007 | Cervantes ..................... 600/534 |

FOREIGN PATENT DOCUMENTS

WO WO9305582 3/1993
WO WO0241489 5/2002

OTHER PUBLICATIONS

Sony NTM-910 900 MHz BabyCall Nursery Monitor, pp. 1-2.

* cited by examiner

*Primary Examiner* — Daniel Wu
*Assistant Examiner* — Emily C Terrell

(57) ABSTRACT

There is provided a baby monitoring system comprising a baby unit and a parent unit, the baby unit being for use in the vicinity of a baby or child, the baby unit detecting noise and transmitting a corresponding stream of audio samples to the parent unit, the parent unit comprising a visual indicator; and a processor for analyzing the stream of audio samples to determine a noise history and for providing a first control signal to the visual indicator such that the visual indicator provides a visual indication of the noise history.

12 Claims, 2 Drawing Sheets

US 8,314,696 B2

BABY MONITORING SYSTEMS

TECHNICAL FIELD OF THE INVENTION

The invention relates to baby monitoring systems, and in particular to baby monitoring systems that provide an indication of noise or activity of a baby or child from a baby unit to a parent unit.

BACKGROUND TO THE INVENTION

Baby monitoring systems are becoming increasingly popular, and these systems generally comprise a baby unit that is placed close to a baby or child to be monitored, and a parent unit that communicates with the baby unit to provide a parent with information about the status of their baby. For example, the most common baby monitor systems have a microphone in the baby unit for picking up sounds (such as the baby crying), and these sounds are sent to the parent unit where they are broadcast for the parent to hear.

In many of these baby monitoring systems, the parent unit is also provided with a visual indicator, such as a series of lights, that gives the parent a visual indication of the level of noise or activity at the baby unit.

One such example is the Philips SCD499 baby monitor, in which a series of LEDs are provided on the parent unit to indicate if the baby has made a noise or cries. As the volume of noise made by the baby increases, more LEDs on the parent unit are switched on.

However, these monitoring systems suffer from the disadvantage that it is easy to miss an indication (whether visual or audible) that the baby has made a noise or has cried if the parent is away from the parent unit briefly (for example getting coffee from the kitchen or going into the garden), or if there is other ambient noise around the parent and/or if the parent unit is not directly in the parent's line of sight (for example when the parent is watching television).

It is therefore desirable to provide a baby monitoring system that does not suffer from this disadvantage.

SUMMARY OF THE INVENTION

Thus, in accordance with the invention, there is provided a baby monitoring system comprising a baby unit and a parent unit, the baby unit being for use in the vicinity of a baby or child, the baby unit detecting noise and transmitting a corresponding stream of audio samples to the parent unit, the parent unit comprising a visual indicator; and a processor for analyzing the stream of audio samples to determine a noise history and for providing a first control signal to the visual indicator such that the visual indicator provides a visual indication of the noise history.

Preferably, the parent unit further comprises a second visual indicator, and the processor is further adapted to analyze the stream of audio signals to determine a current noise level and to provide a respective control signal to the second visual indicator such that the second visual indicator provides a visual indication of the current noise level.

Alternatively, the processor is further adapted to analyze the stream of audio signals to determine a current noise level and to provide a second control signal to the visual indicator such that the visual indicator further provides a visual indication of the current noise level.

In this embodiment, the visual indicator provides a first visual indication for the noise history and a second visual indication for the current noise level.

Preferably, the visual indicator comprises a plurality of lights or LEDs and the visual indication comprises none or one or more illuminated lights or LEDs.

Preferably, each light or LED corresponds to a period of time, and the processor is adapted to generate the first control signal such that a respective light or LED is illuminated in the event that the noise history indicates a noise occurred in the respective corresponding period of time.

In alternative embodiments, the visual indicator comprises a LCD panel.

Preferably, the noise history comprises an indication of the level of noise during one or more time periods.

Preferably, the parent unit further comprises a memory for storing the determined noise history.

Preferably, the parent unit further comprises a speaker, and the processor is further adapted to convert the audio samples into sound for playing through the speaker.

In accordance with a second aspect of the invention, there is provided a method of operating a parent unit in a baby monitoring system, the method comprising receiving a plurality of audio samples; analyzing the audio samples to determine a noise history; and providing an indication of the noise history to a user of the parent unit.

Preferably, the step of providing an indication of the noise history comprises providing a visual indication of the noise history.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
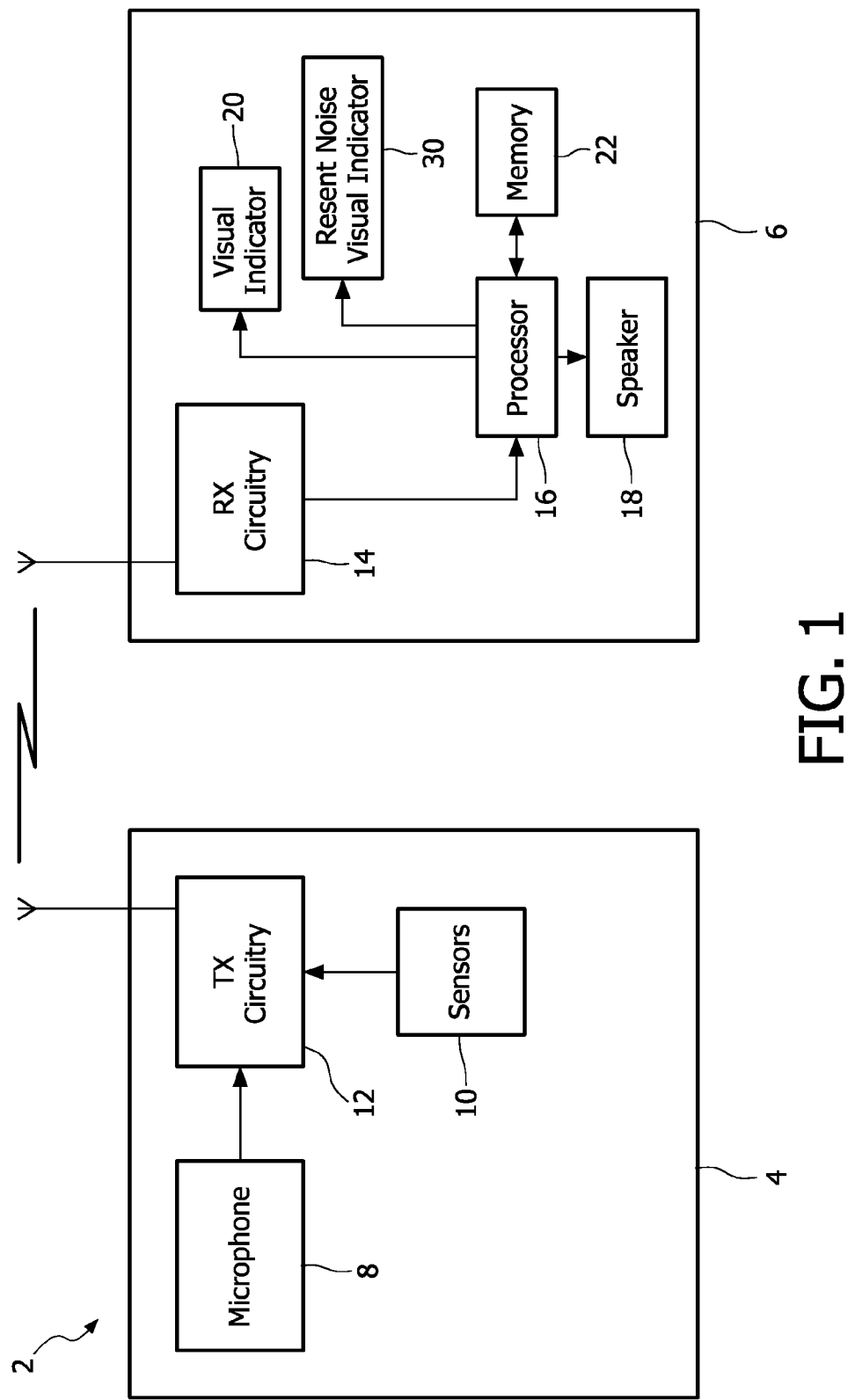
FIG. 1 is a block diagram of a baby monitoring system in accordance with the invention.

FIG. 1 shows a block diagram of a baby monitoring system 2 in accordance with an aspect of the invention. The system comprises a transmission unit 4 in the form of a baby unit that is placed in the vicinity of a baby or child to be monitored, and a receiving unit 6 that is carried or used by a parent remotely from the baby unit 4.

The baby unit 4 comprises a microphone 8 for recording audio in the vicinity of the baby unit 4, and one or more other sensors 10 for sensing conditions at the baby unit 4, such as temperature. The audio from the microphone 8 and data from the sensors 10 is provided to transmitter circuitry 12 which transmits the audio and data to corresponding receiver circuitry 14 in the parent unit 6.

The receiver circuitry 14 provides the received audio and data to a simple processor 16 that controls the parent unit 6. The audio is provided by the processor 16 to a speaker 18 for presentation to a user of the parent unit 6. In addition, the processor 16 converts the received audio samples into a visual representation, and provides this visual representation to a visual indicator 20.

As is conventional, the visual indicator 20 can comprise a series of lights or LEDs, with the number of lights or LEDs illuminated increasing as the level of noise (i.e. the volume of noises such as crying) in the audio stream increases. In this type of visual indicator, each light or LED can have an associated noise threshold, which means that that particular light or LED will be lit when the noise in the audio stream exceeds that threshold. Therefore, when the visual indicator 20 comprises, say, ten lights, and the level of noise in the audio stream is below all thresholds, no lights will be lit. However, when the level of noise is above the highest threshold, all ten lights will be lit. If the level of noise falls between the highest and lowest thresholds, an appropriate number of lights or LEDs will be lit.

A slight modification to this scheme is possible by which only one light or LED is lit, with the particular light or LED being lit based on the level of noise in the audio stream.

In either case, the processor 16 can analyze the received audio stream to determine which noise thresholds have been exceeded and provide the appropriate control signals to the visual indicator 20.

Although the visual indicator 20 can be a simple series or lights, it will be appreciated that it is possible for the visual indicator 20 to be a more complex component, such as an LCD panel.

In accordance with the invention, the parent unit 6 further comprises a memory 22 for storing a recent noise history from the baby unit 4. The processor 16 determines the recent noise history from the received audio samples, and stores the noise history in the memory 22. The processor 16 uses this stored noise history to generate an additional control signal for a visual indicator that controls the visual indicator to provide a visual indication of the noise history.

The processor 16 can determine the noise history by analyzing the audio samples to determine the maximum noise level for a particular time unit (which does not have to correspond to the sampling interval used by the baby unit 4 to generate the audio sample stream).

In preferred embodiments, another visual indicator 30 provides the visual indication of the recent noise history at the same time as visual indicator 20 provides the visual indication of the current noise level. As with visual indicator 20, this additional visual indicator 30 can comprise a series of lights or LEDs, or can be a more complex component, such as an LCD panel. When the visual indicator 30 comprises a series of lights or LEDs, each light or LED preferably represents and shows the noise history for a particular period of time (for example a minute). If, say, the visual indicator 30 comprises five lights or LEDs, each light or LED can correspond to one minute in the preceding five minutes.

In alternative embodiments, there may be a single visual indicator 20 that provides the visual indication of the noise history only when selected by a user of the parent unit 6 (for example if a "noise history" function is selected by the user), and indicates the current noise level at all other times.

Preferably, the memory 22 only stores the noise history covering a short period of time, say ten minutes. In this case, for each of the ten minutes that have elapsed, the memory 22 contains the maximum noise level reached. Of course, as time passes, the memory 22 will be updated by removing the "oldest" maximum noise level.

Figure 2:
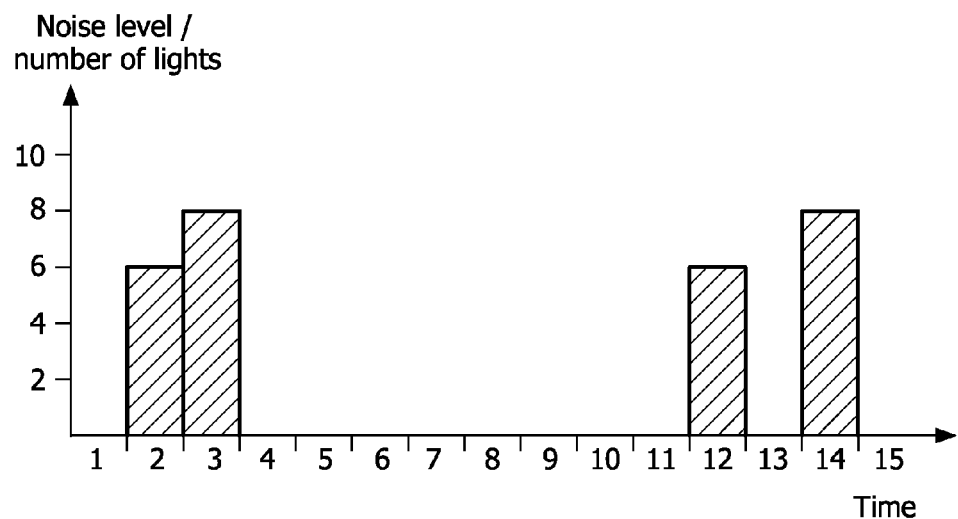
FIG. 2 is a graphical illustration of a situation in which the present invention can be used.

FIG. 2 is a graphical illustration of a situation in which the present invention can be used. In this example, at time 2 and 3, the baby makes a noise that registers at levels 6 and 8 respectively. If the parent leaves the room at time 10 and returns at time 15, he/she will have missed the noises that occurred at times 12 and 14.

However, in accordance with the invention, the noise levels at times 12 and 14 (and 2 and 3 if the memory 22 is large enough) will be stored in the memory 22, and the processor 16 can use this stored history to provide an appropriate control signal to the visual indicator 30.

Figure 3A:
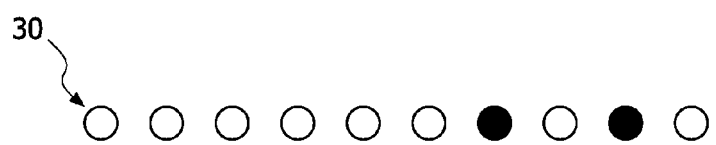
FIG. 3 illustrates the operation of the invention with reference to a visual indicator that comprises ten LEDs.

FIG. 3 illustrates the operation of the invention with reference to a visual indicator 30 that comprises ten LEDs. In FIG. 3(a), the visual indicator 20 is indicating a noise history that corresponds to that shown by the graph in FIG. 2.

In particular, in this example, the right-most LED corresponds to the noise level in the previous minute, whereas the left-most LED corresponds to the noise level in the earliest recorded minute (so ten minutes ago). Therefore, at time 15 in FIG. 2, the seventh and ninth LEDs (counted from the left) of the visual indicator 30 will be lit, indicating that a noise occurred at time 12 (three minutes ago) and time 14 (one minute ago).

Figure 3B:
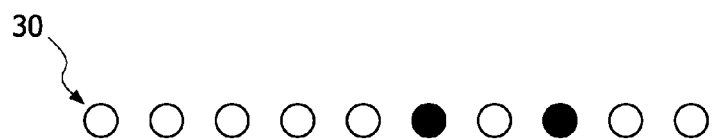

As time elapses, the light pattern shown by the visual indicator 30 can shift to the left at the rate of one LED per minute. Thus, one minute after the visual indication in FIG. 3(a), the sixth and eighth LEDs in the visual indicator 30 will be lit, as shown in FIG. 3(b), rather than the seventh and ninth LEDs.

In further embodiments, the colors of the lights or LEDs indicating respective noise levels (whether historic noise levels or current noise levels) can be different. For example, LEDs indicating a low noise level can be green, LEDs indicating intermediate noise levels can be orange, while LEDs indicating higher noise levels can be red.

As described above, in embodiments of the invention in which the visual indicator 30 is an LCD panel, the visual indication of the historic noise level can be presented as a graph (similar to that shown in FIG. 2) or in any other suitable format. For example, the LCD display can show the noise level as a series of bars that operate in a similar way to the series of lights described above.

It will be appreciated that the processor 16 can analyze the stored noise history and generate the control signal by executing an appropriate software program stored in the memory 22 or within the processor 16 itself. It will further be appreciated that the processor 16 can include a timer module for determining how long particular noise levels are to be stored in the memory 22.

There is therefore provided a baby monitoring system that overcomes the disadvantages with conventional baby monitoring systems.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope. A computer program may be stored/distributed on a suitable medium, such as an optical storage medium or a solid-state medium supplied together with or as part of other hardware, but may also be distributed in other forms, such as via the Internet or other wired or wireless telecommunication systems.

The invention claimed is:

1. A baby monitoring system comprising a baby unit and a parent unit, the baby unit being for use in the vicinity of a baby or child, the baby unit detecting noise and transmitting a corresponding stream of audio samples to the parent unit, the parent unit comprising:

a visual indicator; and a processor for analyzing the stream of audio samples to determine a noise history including a maximum noise level for each of a plurality of time periods and for providing a first control signal to the visual indicator such that the visual indicator provides a visual indication of the maximum noise level for each of the plurality of time periods.

2. The baby monitoring system as claimed in claim 1, wherein the parent unit further comprises a second visual indicator, and the processor is further adapted to analyze the stream of audio signals to determine a current noise level and to provide a respective control signal to the second visual indicator such that the second visual indicator provides a visual indication of the current noise level.

3. The baby monitoring system as claimed in claim 1, wherein the processor is further adapted to analyze the stream of audio signals to determine a current noise level and to provide a second control signal to the visual indicator such that the visual indicator further provides a visual indication of the current noise level.

4. The baby monitoring system as claimed in claim 3, wherein the visual indicator provides a first visual indication for the noise history and a second visual indication for the current noise level.

5. The baby monitoring system as claimed in claim 1, wherein the visual indicator comprises a plurality of lights or Light Emitting diodes (LEDs) and the visual indication comprises none or one or more illuminated lights or LEDs.

6. The baby monitoring system as claimed in claim 5, wherein each light or LED corresponds to a period of time, and the processor is adapted to generate the first control signal such that a respective light or LED is illuminated in the event that the noise history indicates a noise occurred in the respective corresponding period of time.

7. The baby monitoring system as claimed in claim 1, wherein the visual indicator comprises a Liquid Crystal Display (LCD) panel.

8. The baby monitoring system as claimed in claim 1, wherein the visual indicator comprises a plurality of lights or Light Emitting diodes (LEDs) and colors of the lights or LEDs indicate respective noise levels as the visual indication of the maximum noise level during one or more time periods.

9. The baby monitoring system as claimed in claim 8, wherein the processor is configured to control the visual indicator to:

provide a green color to indicate a low noise level during a given time period, provide an orange color to indicate an intermediate noise level during a given time period, and provide a red color to indicate a noise level higher than the intermediate noise level during a given time period.

10. The baby monitoring system as claimed in claim 1, wherein the parent unit further comprises a speaker, and the processor is further adapted to convert the audio samples into sound for playing through the speaker.

11. A method of operating a parent unit in a baby monitoring system, the method comprising:

receiving a plurality of audio samples;

analyzing the audio samples to determine a noise history including a maximum noise level for each of a plurality of time periods; and providing an indication of the maximum noise level for each of the plurality of time periods to a user of the parent unit.

12. The method as claimed in claim 11, wherein the step of providing an indication of the noise history comprises providing a visual indication of the noise history.

* * * * *